(12) United States Patent
Avni et al.

(10) Patent No.: US 6,447,444 B1
(45) Date of Patent: Sep. 10, 2002

(54) VIDEO RECTOSCOPE

(75) Inventors: Arie Avni, Rehovot; Victor Levin, Haifa; Dan Oz, Even Yehuda, all of (IL)

(73) Assignee: Sightline Technologies Ltd., Haifa (IL)

( * ) Notice: Subject to any disclaimer, the term of this patent is extended or adjusted under 35 U.S.C. 154(b) by 0 days.

(21) Appl. No.: 09/530,717

(22) PCT Filed: Nov. 2, 1998

(86) PCT No.: PCT/IL98/00529
§ 371 (c)(1),
(2), (4) Date: Jul. 31, 2000

(87) PCT Pub. No.: WO99/23812
PCT Pub. Date: May 14, 1999

(30) Foreign Application Priority Data

Nov. 4, 1997 (IL) .................................................. 122111

(51) Int. Cl.⁷ .............................. A61B 1/05; A61B 1/012
(52) U.S. Cl. ...................... 600/121; 600/114; 600/109; 600/129; 600/156; 600/159
(58) Field of Search ................................ 600/114, 121, 600/129, 152, 122, 109, 156, 170, 171, 159

(56) References Cited

U.S. PATENT DOCUMENTS

| | | | |
|---|---|---|---|
| 3,677,262 A | 7/1972 | Zukowski | |
| 4,858,001 A | * 8/1989 | Milbank et al. | ............ 348/335 |
| 4,878,485 A | 11/1989 | Adiar | |
| 4,884,133 A | 11/1989 | Kanno et al. | |
| 4,893,613 A | * 1/1990 | Hake | ......................... 600/144 |
| 5,051,824 A | 9/1991 | Nishigaki | |
| 5,201,908 A | * 4/1993 | Jones | ......................... 600/123 |
| 5,203,319 A | 4/1993 | Danna et al. | |
| 5,301,061 A | * 4/1994 | Nakada et al. | ................. 348/75 |
| 5,408,992 A | 4/1995 | Hamlin et al. | |
| 5,489,256 A | 2/1996 | Adiar | |
| 5,538,497 A | 7/1996 | Hori | |
| 5,674,182 A | * 10/1997 | Suzuki et al. | ................ 600/121 |
| 5,817,015 A | * 10/1998 | Adair | ......................... 600/121 |
| 6,007,484 A | * 12/1999 | Thompson | .................. 600/122 |
| 6,110,103 A | * 8/2000 | Donofrio | ..................... 600/114 |
| 6,110,104 A | * 8/2000 | Suzuki et al. | ................ 600/121 |
| 6,132,211 A | * 10/2000 | Peithman | ..................... 433/29 |
| 6,165,123 A | * 12/2000 | Thompson | ................... 600/114 |

OTHER PUBLICATIONS

Catalogue, KleeSpec® Disposable Anoscope, Welch Allyn, Inc., Skaneateles Falls, NY., Jul. 1995.
Catalogue, 24911 S Video Rectoscope, Karl Storz–Endoskope Gmbh, Tuttlingen, Germany Jan. 1996.
Catalogue, Pentax ES–3801 PVE Video Sigmoidoscope, Asahi Optical Co., Tokyo, Japan.

* cited by examiner

*Primary Examiner*—John P. Leubecker
(74) *Attorney, Agent, or Firm*—Pillsbury Winthrop LLP

(57) ABSTRACT

A video endoscope includes a generally rigid; elongate insertion member having distal and proximal ends, and a video camera head fixed at the distal end of the insertion member. A sheath fits over and covers the insertion member, the sheath having a distal portion covering the video camera head, at least a section of which distal portion is substantially transparent. The distal portion of the sheath further including a narrowed tip comprising two or more leaves which are closed during insertion through the anus and open apart after insertion to expose the transparent section of the distal portion of the sheath.

5 Claims, 8 Drawing Sheets

VIDEO RECTOSCOPE

This application is the national phase of international application a PCT/IL 98/00529 filed Nov. 2, 1998 which designated the U.S.

FIELD OF THE INVENTION

The present invention relates generally to medical probes, and specifically to endoscopes.

BACKGROUND OF THE INVENTION

Various types of endoscopes are known in the art for visual inspection and diagnosis of the rectum and sigmoid of the large intestine. Rigid rectoscopes and sigmoidoscopes are most commonly used for this purpose, since they are durable, easy to use and relatively inexpensive.

To perform an examination using the rigid rectoscope (or sigmoidoscope), the physician first inserts a speculum through the anus. An obturator, having a blunt, rounded distal end, is fitted inside the speculum and protrudes distally therefrom to ease the insertion. Once the speculum is in place, the physician withdraws the obturator and closes the proximal end of the speculum with a plug. A special telescope is fitted into the plug, which enables the physician to view the inside of the rectum and sigmoid at the distal end of the speculum, either by direct vision or using a video camera coupled proximally to the telescope. In order to illuminate the area under view, a light source in an external console is coupled proximally to the speculum by fiberoptics. Typically, the plug also includes one or more working channels, which are used for irrigation, insufflation or insertion of surgical tools through the speculum.

Various rectoscopes and sigmoidoscopes of this type are available commercially. For example, Karl Storz GmbH, of Tuttlingen, Germany, offers the model 24911S rectoscope, which may be used with a rod lens telescope (for example, model 24946B) to view the rectum either under direct view or using a Karl Storz Endovision video camera. The rectoscope and accessories are made from stainless steel to allow disinfection and autoclaving between uses.

Rectoscopes and sigmoidoscopes having a disposable speculum and obturator are also available, such as the KleenSpec disposable sigmoidoscope produced by Welch Allyn Inc., of Skaneateles Falls, N.Y. The speculum and obturator are made of plastic. The speculum clips or screws onto a multi-use handle, to which a light source, telescope, video camera and instruments may be attached.

Flexible sigmoidoscopes and colonoscopes are also known in the art. Most such scopes include a fiberoptic bundle for conveying images from their distal end, within the intestine, to an eyepiece or video camera fixed to the proximal end. Some such scopes, such as the Pentax ES3801 PVE Video Sigmoidoscope, made by Asahi Optical Company of Tokyo, have a CCD detector with an objective lens at its distal end. By comparison with rigid rectoscopes and sigmoidoscopes, however, flexible scopes are costly, fragile and difficult to clean.

SUMMARY OF THE INVENTION

It is an object of some aspects of the present invention to provide an improved endoscope, and particularly an improved rectoscope.

It is an object of some aspects of the present invention to provide a video rectoscope that gives improved visibility of anatomical features within the rectum.

It is another object of some aspects of the present invention to provide a rectoscope that is easy and convenient for medical personnel to use.

It is a further object of some aspects of the present invention to provide a rectoscope including an easily-replaceable disposable portion, thus minimizing or eliminating the need for disinfection and sterilization between uses.

It is yet another object of some aspects of the present invention to provide methods and apparatus that facilitate insertion of an endoscope, particularly a rectoscope or sigmoidoscope, into a body cavity.

It is still another object of some aspects of the present invention to provide an improved steering mechanism for an endoscope.

In preferred embodiments of the present invention, a rectoscope comprises an elongate, generally rigid insertion member having a video camera head at its distal end. The insertion member and camera head are covered by a disposable sheath, which includes a transparent distal portion, preferably including an optical window, covering the camera head. The camera head includes an image detector array, preferably a CCD array, as is known in the art, along with a light source for illuminating an area of the intestine viewed by the camera head and an objective lens, which focuses an image of the area onto the array. The sheath, which is preferably made of a biocompatible plastic material, is removed and discarded after use. The rectoscope is used to examine and treat areas of the colon of a patient, specifically the rectal and sigmoid portions of the colon.

By comparison with rigid rectoscopes and sigmoidoscopes known in the art, the present invention can provide substantially improved image quality, because the video camera head is placed at the distal end of the rectoscope, near the area under view. The distal positioning of the camera head enables the present rectoscope to achieve both higher magnification and a wider field of view than video rectoscopes and sigmoidoscopes known in the art, in which the camera head views the intestine through a telescope from the proximal end of the scope.

In preferred embodiments of the present invention, the sheath comprises a narrowed, generally bluntly pointed tip, to ease insertion of the rectoscope through the anus. The narrowed tip thus performs the function of the obturator used in insertion of rectoscopes and sigmoidoscopes known in the art. Elimination of the obturator relieves a physician using the rectoscope of unpleasant odors and possible exposure to infection that are commonly associated with removal of the obturator.

In some preferred embodiments of the present invention, the optical axis of the camera head is angled relative to the longitudinal axis of the insertion member, and the distal end of the sheath is likewise angled, thus defining the narrowed tip. Preferably, the sheath has a bulbous protrusion at the tip, which further eases insertion of the rectoscope through the anus.

In one such preferred embodiment, a mirror is fixed to the bulbous protrusion, which is shaped so that the mirror is positioned within the field of view of the camera head and is oriented obliquely relative to the optical axis thereof An image of the inner wall of the rectum or sigmoid is reflected from the mirror and captured by the camera head. The mirror thus enables the physician to see an image from an alternative view angle, which may be useful particularly in observing and controlling the movement of tools that the physician inserts into the rectum using the rectoscope, as described below.

In other preferred embodiments of the present invention, the narrowed tip of the sheath is formed by a plurality of leaves, formed of a resilient material, which butt together tightly in a closed configuration to cover the transparent portion of the sheath and the camera head. During insertion through the anus, the closed leaves protect the transparent portion from fouling by fecal matter, lubricants or other substances. After the rectoscope has been inserted, the leaves are drawn apart, preferably by pulling the sheath back proximally, so as to expose the transparent portion of the sheath and allow the camera head to receive images of the area of the intestine under view.

In some preferred embodiments of the present invention, the sheath includes one or more worldling channels, which may be used for suction, irrigation, insulation, passage of surgical tools or other functions known in the art. The rectoscope includes a handle, to which the sheath is attached, preferably by a quick connect/disconnect fitting. Preferably, the handle includes user controls for regulating such functions as suction, irrigation and insufflation through the working channels. Further preferably, one or more of the working channels include a one-way valve, to prevent back-flow of fluid (gas or liquid) used in irrigation or insufflation through the channels.

Although rectoscopes in accordance with the present invention are described herein as being generally rigid, in some preferred embodiments the insertion member may include a flexible, resilient longitudinal section. This section allows the rectoscope to bend during insertion into the rectum, to make the insertion easier and less painful for the patient. Such bending is not possible using rigid endoscopes known in the art, and it differs from the bending of flexible endoscopes, which do not have the rigidity to maintain a particular shape and require complex steering mechanisms to control their angle and direction of bend.

In one such preferred embodiment, the rectoscope sheath comprises one or more flexible, longitudinally-disposed inflatable bladders, preferably at least two such bladders disposed radially within the sheath on different sides of the flexible section of the insertion member. Preferably, the bladders are placed on opposing sides of the sheath. The bladders are connected by respective valves to a suitable pressure source. When the pressure in one of the bladders is increased, the bladder lengthens, whereas when the pressure is decreased, the bladder tends to shorten. Thus, the bend angle of the sheath and of the insertion member therein is controlled by varying the pressure in the one or more bladders.

In another preferred embodiment of the present invention, a generally rigid rectal insert having a curved channel therethrough is inserted into the rectum, up to the sigmoid flexure. The insert is turned within the rectum so that the exit from the channel at the sigmoid flexure opens into the intestine in a direction generally along the axis of the sigmoid. The rectoscope including the flexible section, as described hereinabove, is then inserted through the channel and is forced by the rigidity of the insert to bend toward the sigmoid axis. The combination of the insert and rectoscope, in accordance with this preferred embodiment, thus allows endoscopic inspection of a portion of the intestine that can generally be reached only using a more costly flexible endoscope. The rectal insert described herein can also be used in conjunction with flexible endoscopes known in the art, making it easier to pass the endoscope through the sigmoid and reducing pain and the possibility of accidental perforation of the intestine.

Although preferred embodiments are described herein with reference to inspection and treatment of the rectum, and endoscopes in accordance with such preferred embodiments are referred to herein generally as rectoscopes, it will be appreciated that such endoscopes may similarly be adapted and applied to serve as sigmoidoscopes. The principles of the present invention may similarly be applied to produce rigid endoscopes for insertion into other body cavities, such as the throat, the vagina, or any other cavity large enough to receive an endoscope having a video camera head at its distal end, as described herein.

There is therefore provided, in accordance with a preferred embodiment of the present invention, a video endoscope, including:

a generally rigid, elongate insertion member, having distal and proximal ends;

a video camera head fixed at the distal end of the insertion member, and a sheath, which fits over and covers the insertion member, the sheath having a distal portion covering the video camera head, at least a section of which distal portion is substantially transparent.

Preferably, the camera head includes a detector array and an objective lens, which forms an image on the detector array.

In a preferred embodiment, the camera head is inclined obliquely relative to a longitudinal axis of the insertion member.

Preferably, the camera head includes a light source, most preferably including one or more LEDs.

Preferably, the substantially transparent section of the distal portion of the sheath includes an optical window.

Preferably, the distal portion of the sheath includes a narrowed tip, which facilitates insertion of the endoscope through the anus. Further preferably, the narrowed tip includes a bulbous protrusion.

Alternatively or additionally, the narrowed tip includes two or more leaves, which are closed during insertion through the anus and open apart after insertion to expose the transparent section of the distal portion of the sheath. Preferably, to open the leaves, the sheath is shifted in a proximal direction drawn relative to the insertion member.

Preferably, the sheath contains a worldling channel passing longitudinally therealong. Further preferably, the sheath includes a one-way valve within the worldling channel, for preventing back-flow of fluid therethrough.

Preferably, the endoscope includes a handle, fixed to the proximal end of the insertion member, and the handle includes user controls for controlling the passage of fluid through the working channel.

In a preferred embodiment, at least a longitudinal section of the insertion member is flexible and resilient. Preferably, the sheath includes an inflatable bladder disposed longitudinally within the sheath, such that inflation of the bladder causes its length to increase so that the insertion member bends.

In another preferred embodiment, a mirror is fixed in a position distal to the camera head within a field of view thereof and oriented obliquely relative to an optical axis of the camera head, so that the camera head captures an image reflected from the mirror. Preferably, the image reflected from the mirror includes an area of a physiological structure in which a surgical procedure is to be performed using the endoscope.

There is further provided, in accordance with a preferred embodiment of the present invention, a steering mechanism for an elongate medical probe, including at least one controllably inflatable element fixed to the probe, such that a longitudinal dimension of the element changes responsive to inflation thereof thereby causing the probe to bend.

Preferably, the at least one inflatable element includes two elements disposed radially on different sides of the probe, so as to bend the probe in different, respective directions. Further preferably, the two elements include first and second elements on opposing sides of the probe, such that the first element is inflated and the second element is deflated so as to bend the probe toward the side on which the second element is fixed.

Preferably, the at least one inflatable element includes an expandable wall section on an outer surface thereof, which expands and contracts responsive to changes in the inflation of the element.

Preferably, the mechanism includes a pressure source which is controllably applied to the inflatable element so as control the bending of the probe.

In a preferred embodiment, the probe includes a generally rigid endoscope, having a flexible section which is bent by the mechanism, wherein the endoscope preferably includes a disposable sheath, which includes the at least one inflatable element.

There is moreover provided, in accordance with a preferred embodiment of the present invention, a generally rigid rectal insert, having a distal end which is inserted into the rectum of a patient, the insert having a curved channel therethrough through which an endoscope is inserted into the sigmoid portion of the colon of a patient.

Preferably, the distal end of the insert is brought into proximity with the patient's sigmoid flexure, and the channel is curved so as to open laterally out of the distal end into the flexure. Further preferably, the insert is rotatable within the rectum so as to align the opening of the channel at the distal end thereof with the intestine.

There is also provided, in accordance with a preferred embodiment of the present invention, a method of endoscopic inspection, including:

providing an elongate, generally rigid insertion member having a video camera head at a distal end of the member;

fitting a disposable sheath over the member, such that the camera head is covered by a substantially transparent portion of the sheath;

inserting the insertion member, covered by the sheath, into a body cavity of a subject; and receiving video images within the body cavity from the camera head.

Preferably, fitting the sheath includes fitting a sheath having a narrowed tip, and inserting the member includes first inserting the narrowed tip into the cavity.

In a preferred embodiment, the narrowed tip is opened after insertion to expose the substantially transparent portion of the sheath covering the camera head, wherein opening the narrowed tip preferably includes shifting at least a portion of the sheath in a proximal direction over the insertion member so as to separate two or more leaves that meet to form the narrowed tip.

Preferably, receiving the video images includes illuminating the inside of the body cavity using a light source in the video camera head.

Further preferably, fitting the disposable sheath includes fitting a sheath having at least one working channel passing therethrough. In a preferred embodiment, the body cavity is insufflated by passing a pressurized fluid through the working channel.

In a preferred embodiment, providing the insertion member includes providing a member at least a longitudinal portion of which is flexible and resilient, and inserting the member includes flexing the flexible, resilient portion. Preferably, inserting the member includes inserting an insert into the body cavity having a curved channel therethrough, and passing the member through the channel. Alternatively or additionally, flexing the flexible, resilient portion includes inflating an inflatable bladder disposed within the sheath so that the length of the bladder increases, thereby bending the portion.

Preferably, inserting the insertion member includes inserting the member through the anus of the subject, and receiving the images includes receiving images within the rectum or, alternatively or additionally, receiving images within the sigmoid.

There is further provided, in accordance with a preferred embodiment of the present invention, a method for steering a medical probe, including:

fixing an inflatable element to the probe; and controllably inflating the element so as to change the length thereof, thus causing the probe to bend.

Preferably, fixing the inflatable element includes fixing a plurality of elements on different sides of the probe, so that each element causes the probe to bend in a different, respective direction.

In a preferred embodiment, the medical probe includes a generally rigid endoscope at least a section of which is flexible, and wherein controllably inflating the element causes the flexible section of the endoscope to bend.

There is additionally provided, in accordance with a preferred embodiment of the present invention, a method for inserting an endoscope into the colon of a patient, including:

providing a generally rigid insert having proximal and distal ends and having a curved channel passing therethrough with a lateral opening at the distal end;

inserting the insert into the patient's rectum so that the distal end is in proximity to the sigmoid flexure of the colon; and passing the endoscope through the channel and into the sigmoid colon.

Preferably, the insert is rotated to align the opening at the distal end of the insert with the colon before passing the endoscope therethrough.

Preferably, passing the endoscope includes passing a flexible endoscope through the channel or, alternatively, passing a generally rigid endoscope including a flexible portion through the channel, such that the flexible portion is bent by the curve of the channel.

The present invention will be more fully understood from the following detailed description of the preferred embodiments thereof, taken together with the drawings in which:

DETAILED DESCRIPTION OF PREFERRED EMBODIMENTS

Figure 1:
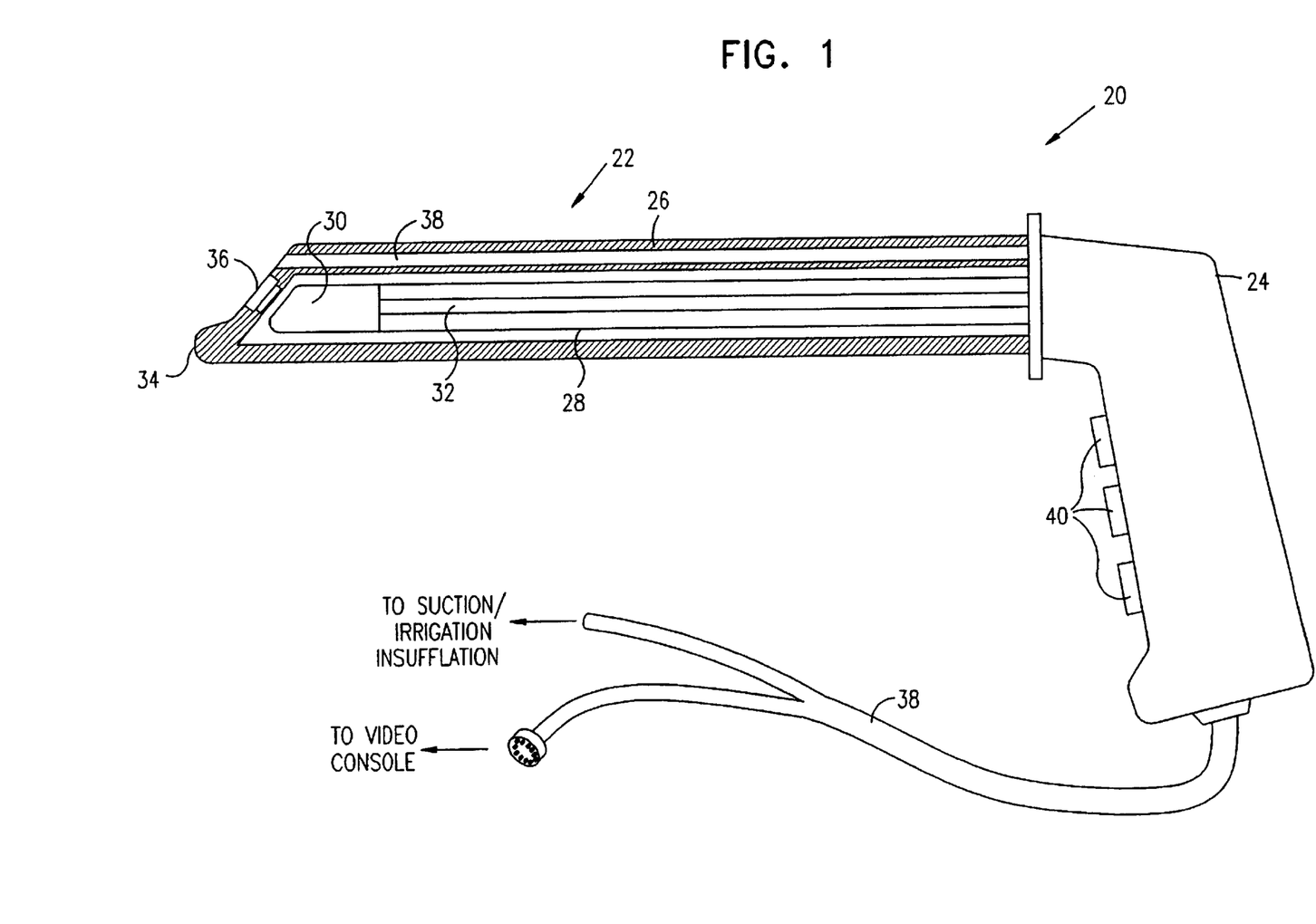
FIG. 1 is a schematic, partly sectional illustration of a rectoscope, in accordance with a preferred embodiment of the present invention.

Reference is now made to FIG. 1, which is a schematic, partly sectional illustration of a video rectoscope 20, in accordance with a preferred embodiment of the present invention. Rectoscope 20 comprises an insertion section 22, which is inserted into the rectum of a subject, and a handle 24, which is grasped by a physician making the examination. Insertion section 22 includes an insertion member 28, fixed to handle 24, and a disposable sheath 26, covering the insertion member. Member 28 includes a video camera head 30 at the member's distal end, connected by wires 32 to handle 24. Preferably, sheath 26 comprises a biocompatible plastic material, such as polycarbonate, and is attached to handle 24 using a quick-connect fitting, as is known in the art. After use, sheath 26 is removed and disposed of.

Figure 2:
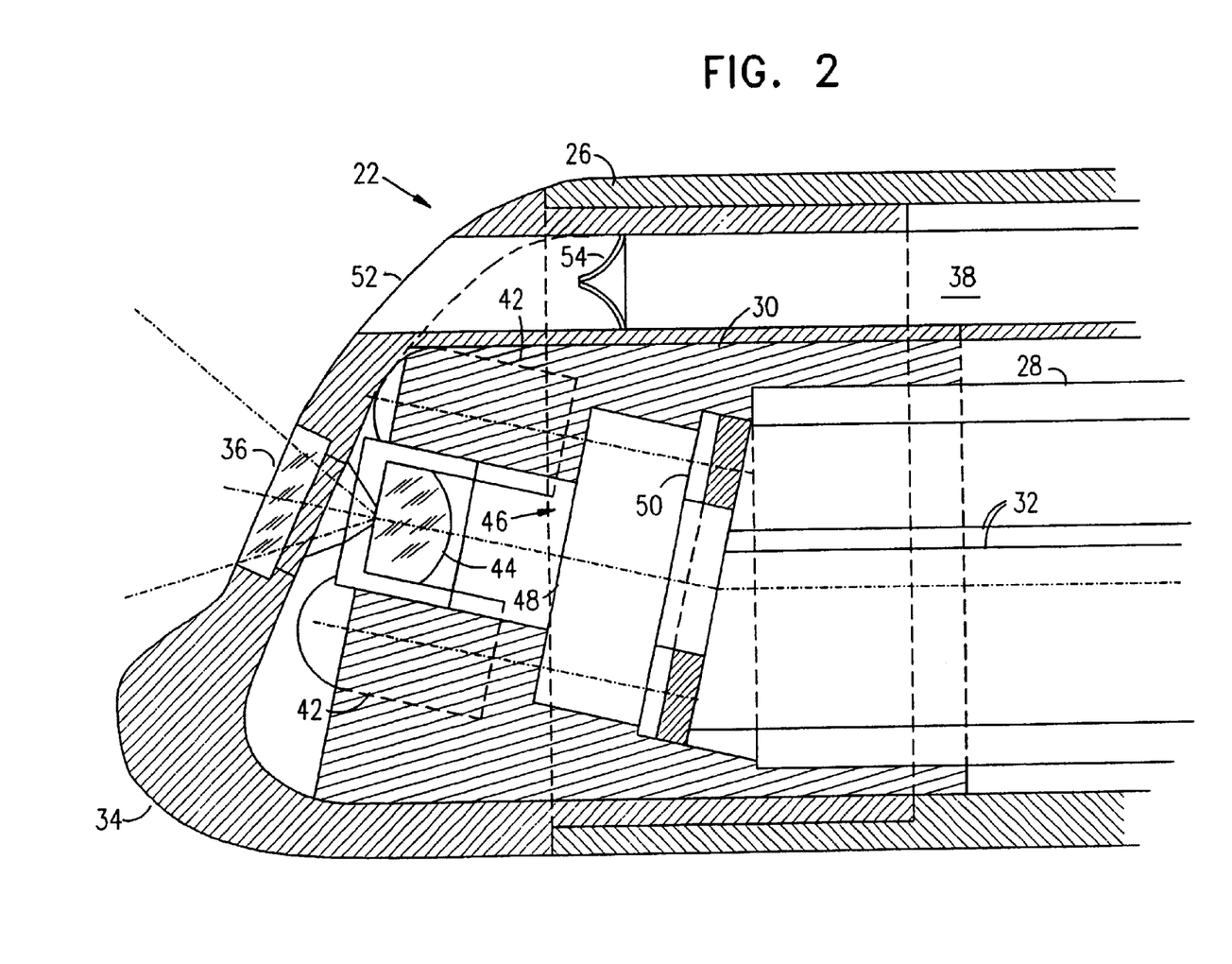
FIG. 2 is a sectional, detail view of a distal portion of the rectoscope of FIG. 1.

FIG. 2 is a schematic, sectional illustration showing details of the distal end of insertion section 22, including camera head 30. The camera head comprises a detector array chip 46, preferably comprising a color CCD array 50, such as a Sony ICX087AKB CCD chip, with a suitable optical filter 48 affixed thereto. One or more lamps 42 illuminate an area of the intestine under view by the camera head. An image of the area is received through an optical window 36 in sheath 26 and focused onto array 50 by an objective lens 44.

Signals generated by chip 46 are conveyed by wires 32 to handle 24, and from there via a cable 38 (FIG. 1) to a video console, where the signals are processed and used to drive a video display. The video console and display (not shown in the figures) use standard video electronics, well known in the art. Alternatively, handle 24 may include a power source, such as one or more batteries, processing electronics and a video transmitter, and convey processed signals from chip 46 to the video console over a wireless link.

Lamps 42 preferably comprise white-light LEDs, such as T1 White L3-W31N LEDs produced by Sloan AG of Basel, Switzerland. The lamps are powered by electrical current conveyed over wires 32 and cable 38 from the console. Alternatively, the lamps may be powered by batteries in handle 24, as described above. In either case, the use of lamps 42 alleviates the complication and expense of using a high-power fiberoptic light source to illuminate the area under view, as in endoscopes known in the art.

Window 36 is shown in FIG. 2 as being relatively small, in order to simplify production and reduce the cost of sheath 26. Sheath 26 also includes a transparent area surrounding the window to allow light from lamps 42 to reach the area under view, but this area need not be of optical quality. In fact, all of sheath 26 may be made of transparent plastic if desired.

It will be observed that the optical axis of lens 44 and array 50 is angled obliquely relative to the longitudinal axis of member 28. Window 36 and the distal end of sheath 26 are similarly angled. This angling allows camera head 30 to view an area of the intestinal wall relatively near the distal end of section 22, rather than pointing straight down the intestine as in rigid rectoscopes and sigmoidoscopes known in the art. As a result of this arrangement, section 22 can be made relatively narrow and pointed at its distal end, so that insertion through the subject's anus is easier and less painful, without the need for a separate obturator. Preferably, a bulbous projection 34 is formed at the distal tip of sheath 26, shaped so as to penetrate the anus with a minimum of discomfort to the patient.

Sheath 26 preferably includes at least one working channel 38, which terminates in an opening 52 at the distal end of the sheath. Channel 38 may be used to inserted surgical tools, such as biopsy forceps, into the intestine and perform surgical procedures under view of camera head 30. The angled orientation of the camera head, as described above, is particularly advantageous for viewing such procedures, since the surgical tool will engage the intestinal wall within the camera head's area of view.

Additionally or alternatively, channel 38 may be used for suction, irrigation and/or insufflation of the intestine, by connecting the channel to a suitable pump or gas source, as is known in the art. Preferably, the connection is made via handle 24, and the suction, irrigation or insufflation is controlled by user controls 40 on the handle. Generally, it is desirable to insufflate the intestine during examination, so as to force the intestinal wall away from window 36 and thus provide camera head 30 with a clearer view of the wall. For this purpose, sheath 26 preferably includes a one-way valve 54, such as a leaflet valve, as is known in the art, in channel 38. After a pressurized gas has been passed through the channel to insufflated the intestine, valve 54 closes to prevent back-flow of the gas and maintain the pressure in the intestine.

Figure 3A:
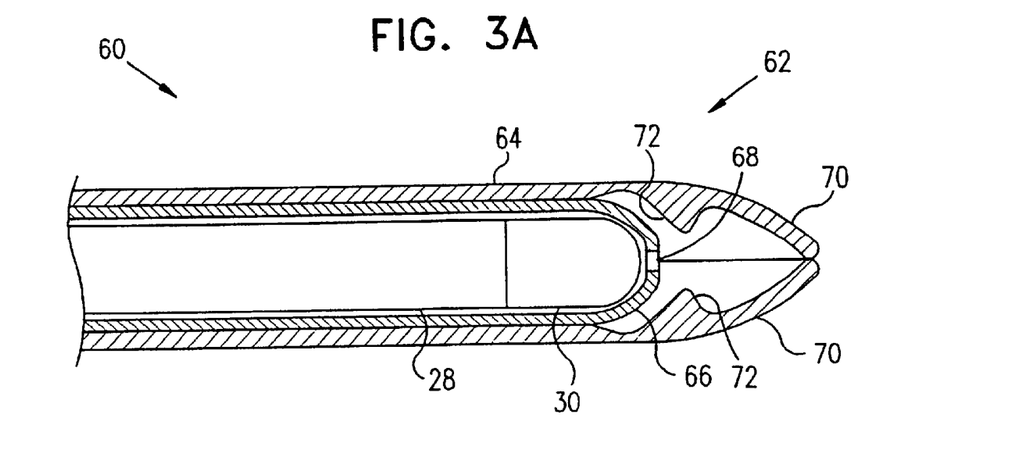
FIGS. 3A and 3B are schematic, sectional illustrations of a rectoscope covered by a sheath in closed and open configurations thereof, respectively, in accordance with another preferred embodiment of the present invention.
Figure 3B:
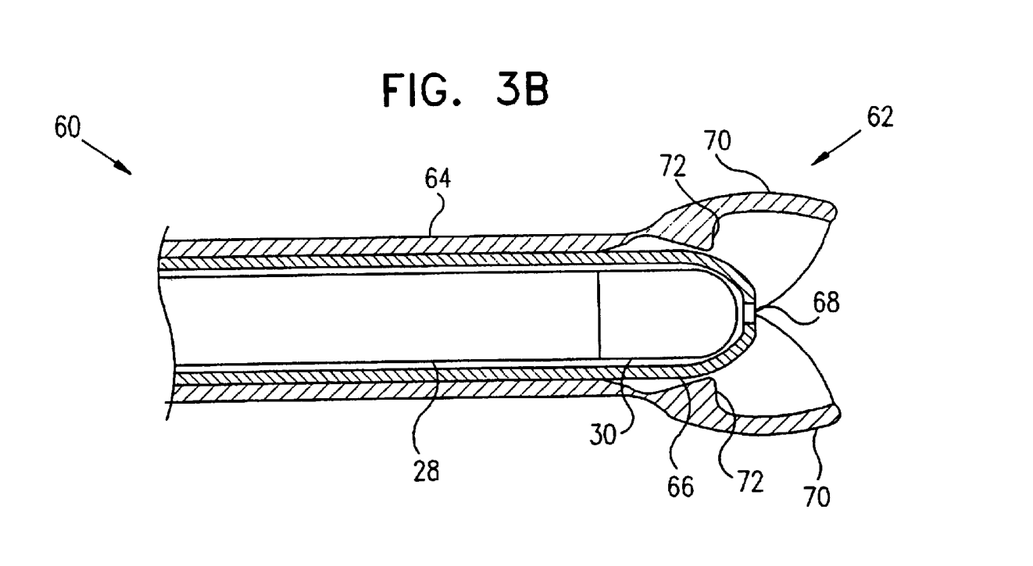

FIGS. 3A and 3B are schematic, sectional illustrations showing a rectoscope 60 including a disposable sheath 62, in accordance with another preferred embodiment of the present invention. Rectoscope 60 includes a generally rigid insertion member 28 with a video camera head 30 at its distal end, substantially as described above with reference to FIGS. 1 and 2, although in rectoscope 60, the optical axis of the camera head is generally aligned with the longitudinal axis of member 28.

Sheath 62 comprises an outer layer 64 and an inner layer 66. The inner layer preferably comprises a generally rigid plastic material, such as polycarbonate, and fits snugly over member 28. Layer 66 includes a transparent distal portion, preferably including an optical window 68, as described above. Outer layer 64 is preferably made of a flexible, resilient plastic, such as polyethylene, and includes two or more leaves 70, preferably three such leaves.

As shown in FIG. 3A, during insertion of rectoscope 60 through the anus, leaves 70 butt together, closing off the distal end of the rectoscope and protecting window 68. The leaves preferably form a bluntly pointed structure, which eases the insertion.

As shown in FIG. 3B, after the insertion, leaves 70 are opened to expose window 68 and allow camera head 30 to receive images of the interior of the intestine. Preferably, the leaves are opened by drawing outer layer 64 in a proximal direction, out of the rectum (to the right in FIGS. 3A and 3B), relative to inner layer 66. Each leaf 70 preferably includes an inner protrusion 72, which engages the surface of inner layer 66 and forces the leaf outward, as shown in the figure. After the rectoscopy procedure is completed, sheath 62 may be returned to the configuration of FIG. 3A for removal through the anus.

Figure 4A:
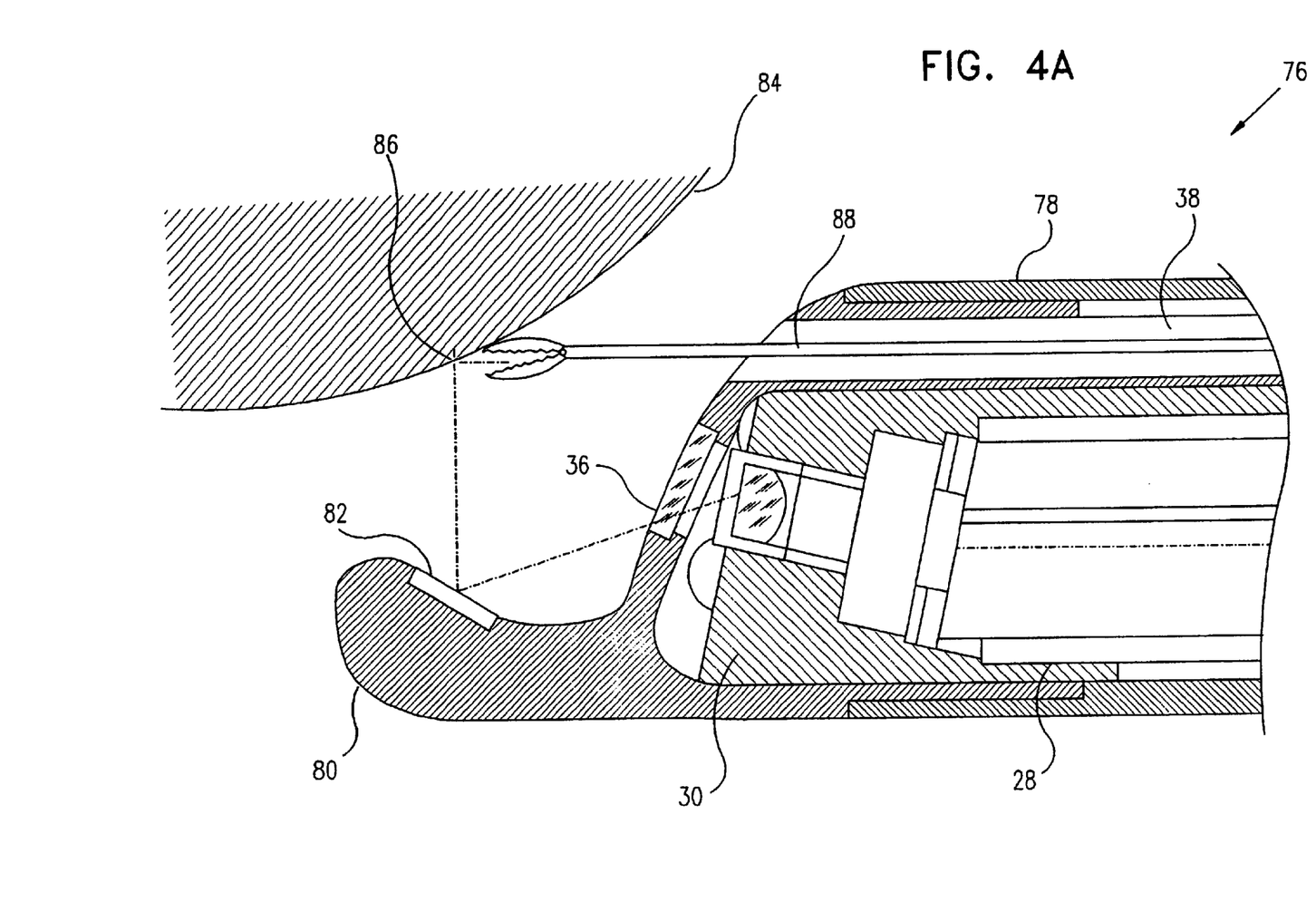
FIG. 4A is a schematic, sectional view of the distal portion of a rectoscope, in accordance with another preferred embodiment of the present invention.

FIG. 4A is a schematic, sectional illustration showing the distal portion of a rectoscope 76, in accordance with another preferred embodiment of the present invention. Rectoscope 76 is generally similar to rectoscope 20, shown in FIGS. 1 and 2, and comprises insertion member 28 with camera head 30 at its distal end. Rectoscope 76 is covered by a sheath 78, similar to sheath 26 except that sheath 78 includes a bulbous protrusion 80 that extends into the field of view of camera head 30. A mirror 82 is fixed to protrusion 80, in such a position and orientation thereon that an image of a physiological structure 84, generally the rectal wall, is reflected from the mirror, through window 36, and is captured by camera head 30. In the example shown in FIG. 4A, a surgical tool 88 is inserted through working channel 38 in sheath 78 and is used to take a biopsy sample at a point 86 on structure 84.

Figure 4B:
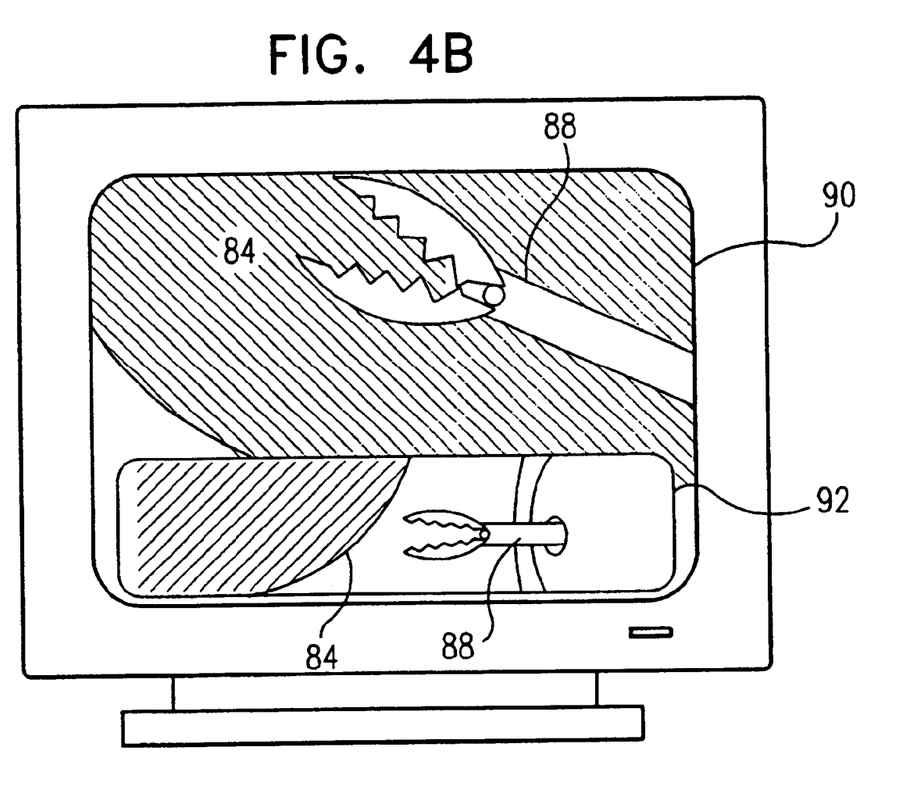
FIG. 4B is a schematic illustration of a video image captured by the rectoscope of FIG. 4A.

FIG. 4B is a schematic illustration showing a video image 90 captured using rectoscope 76 in the configuration of FIG. 4A. The upper part of the image shows tool 88 and structure 84 as seen by camera head 30 directly through window 36. The image of the tool is foreshortened, because of the viewing angle of the camera head. It may therefore be difficult to judge the distance from the tool to the structure based on such an image. An inset 92 in the lower portion of image 90 shows tool 88 and structure 84 as seen via mirror 82. In this case, the angle from which the tool is viewed allows its position and distance from structure 84 to be seen clearly and controlled with greater accuracy.

Figure 5A:
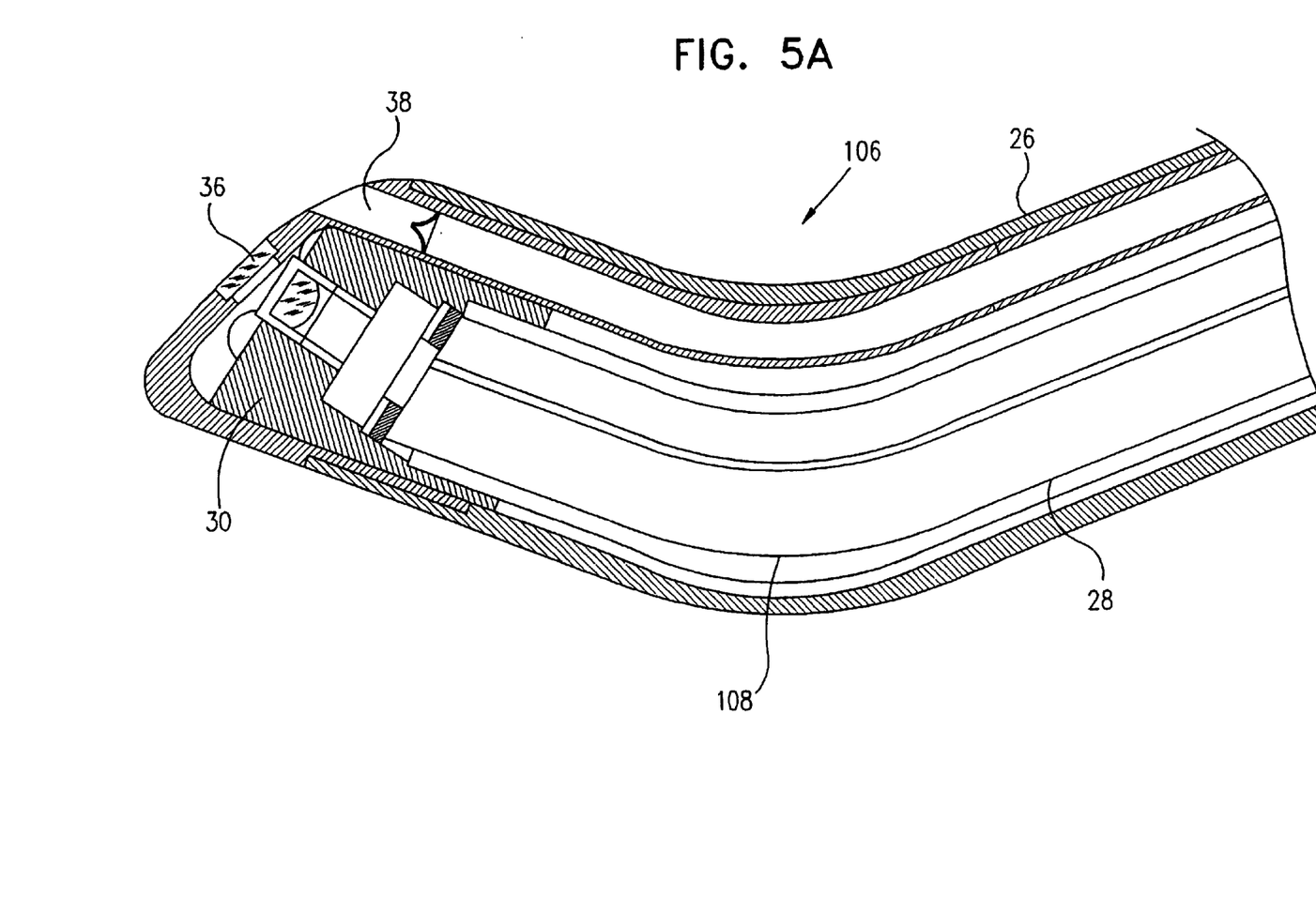
FIG. 5A is a schematic, sectional view of the distal portion of a rectoscope, in accordance with a preferred embodiment of the present invention.

FIG. 5A is a schematic, sectional illustration of the distal portion of a rectoscope 106, in accordance with another preferred embodiment of the present invention. Rectoscope 106 is substantially similar to rectoscope 20, shown in FIGS. 1 and 2, except that insertion member 28 of rectoscope includes at least one flexible, resilient section 108. Section 108 preferably includes an elastic element, for example, a spring steel insert, which normally holds the section straight, but allows it to bend in response to lateral forces exerted thereon. Further preferably, sheath 26 of rectoscope 106 includes flexible, elastic material, for example, polyethylene or silicone, so that the sheath can bend and stretch accordingly when section 108 bends.

The ability of rectoscope 106 to bend allows it to be inserted into the rectum, up to the sigmoid, more easily and with less pain and discomfort to the patient than a fully rigid rectoscope or sigmoidoscope would cause. Rigid endoscopes known in the art cannot have a flexible section like rectoscope 106, since bending of the flexible section would disrupt the optical axis of the telescope that is used for endoscopic viewing. Although flexible sigmoidoscopes known in the art can be bent and inserted with less patient discomfort than rigid scopes, such flexible scopes require complicated and costly steering mechanisms. By placing camera head 30 at the distal end of rectoscope 106, the present invention allows a measure of flexibility without the necessity of a steering mechanism.

Figure 5B:
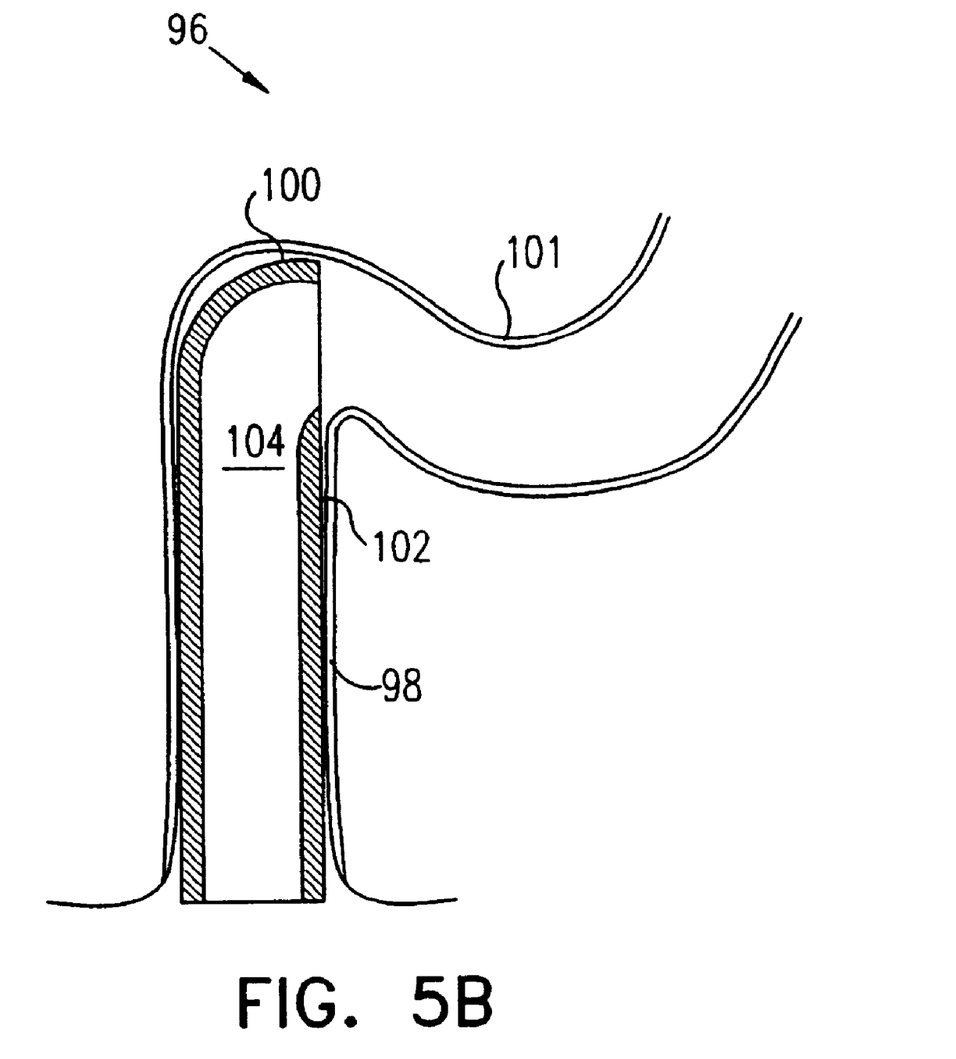
FIG. 5B is a schematic, sectional illustration of a rectal insert, useful particularly in conjunction with the rectoscope of FIG. 5A, in accordance with a preferred embodiment of the present invention.

FIG. 5B is a schematic, sectional illustration showing a rectal insert 102, for use in endoscopic examination and treatment of intestine 96 of a patient, in accordance with a preferred embodiment of the present invention. Insert 102 is particularly useful for guiding rectoscope 106 into the intestine, but may also be used in conjunction with conventional flexible endoscopes known in the art. Insert 102 is preferably made of a generally rigid plastic material, such as polycarbonate, but may be somewhat flexible so as to ease its insertion. The insert has a curved channel 104 passing therethrough, with an inner diameter large enough for an endoscope, such as rectoscope 106, to be inserted through the channel.

Insert 102 is inserted through rectum 98 up to sigmoid flexure 100 of intestine 96. The insert is turned so that channel 104 opens into sigmoid portion 101 of the intestine, as shown in FIG. 5B. Rectoscope 106 is then passed through the insert and bends along the curve in the channel. The distal end of the rectoscope, including camera head 30, is pushed out into sigmoid 101, allowing inspection and treatment of a portion of intestine 96 that would otherwise be accessible only using a conventional flexible endoscope. Insert 102 also protects the area of flexure 100 from pressure due to the rectoscope (or to a conventional flexible endoscope inserted therethrough) that could otherwise cause pain or even perforation of the intestine.

Figure 6:
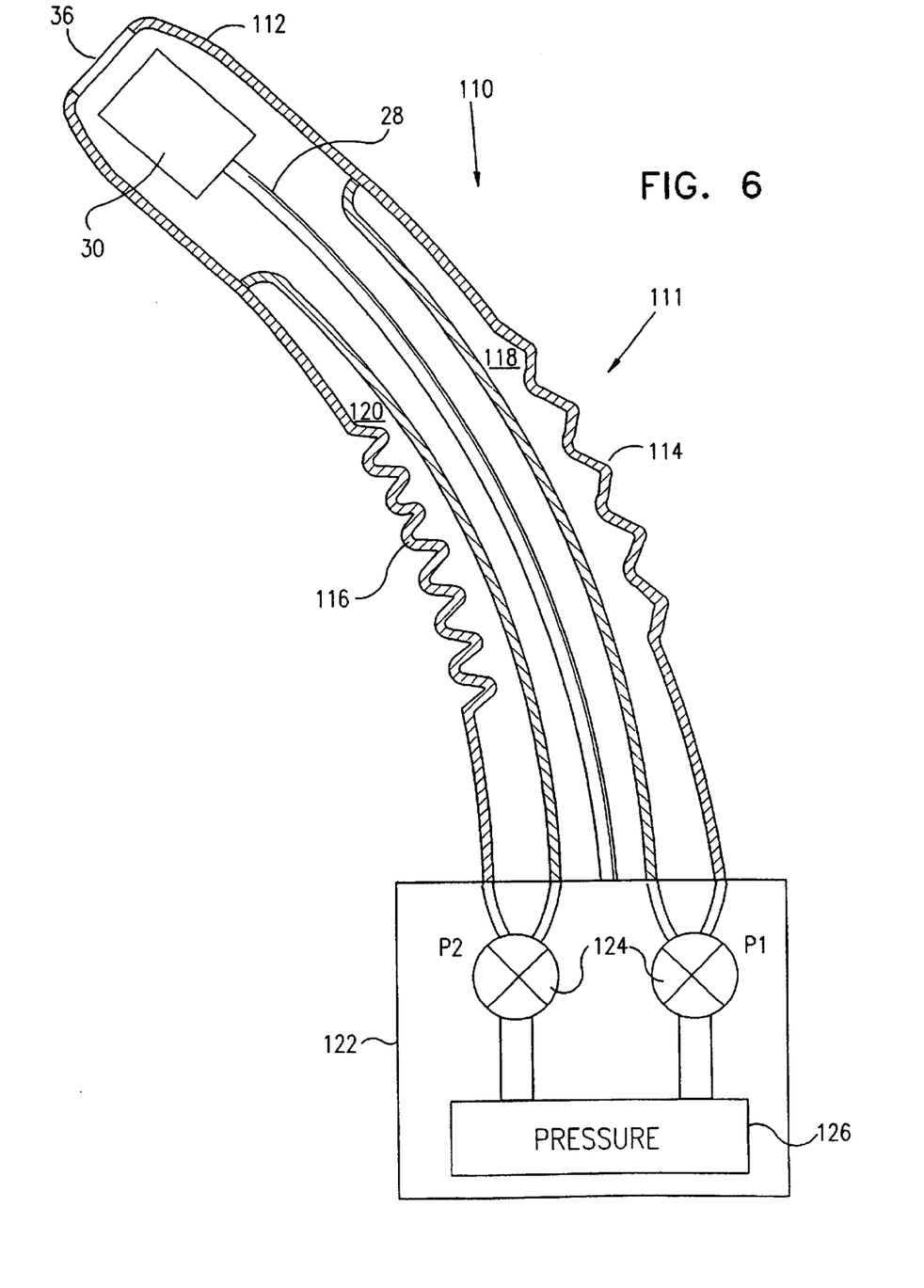
FIG. 6 is a schematic, sectional illustration of a rectoscope, in accordance with still another preferred embodiment of the present invention.

FIG. 6 is a schematic, sectional illustration showing a rectoscope 110, including a steering mechanism 111, in accordance with another preferred embodiment of the present invention. Rectoscope 110 comprises insertion member 28 and camera head 30, covered by a disposable sheath 112 with optical window 36 at a distal end thereon as in other preferred embodiments described above. Member 28 of rectoscope 110 either has a flexible section, as described above with reference to FIG. 5A, or is made flexible over substantially its entire length, as shown in FIG. 6.

Steering mechanism 111 comprises two flexible, elongate bladders 118 and 120, contained within sheath 112 and disposed radially on opposing sides of member 28. Bladders 118 and 120 have respective expandable wall sections 114 and 116, preferably accordion-type walls, as shown in FIG. 6. The bladders are coupled via valves 124 to a pressure source 126, for example, a gas bottle or pump, which may be contained either in a handle 122 of rectoscope 110 or in a separate console. By operating valves 124, bladders 118 and 120 are pressurized to respective pressures P1 and P2. In the example shown in FIG. 6, P1 is greater than P2, causing wall section 114 of bladder 118 to expand, and wall section 116 of bladder 120 to contract, thereby causing member 28 to bend.

Mechanism 111 thus provides a simple, low cost, disposable means for controllably bending and steering rectoscope 110, by inflating and deflating bladders 118 and 120 in sheath 112. Additional bladders may be positioned along the length of the rectoscope and/or radially around it in order to give greater control of the bend shape and direction of the rectoscope. It will be appreciated that such pressure-driven steering mechanisms, either disposable or reusable, can also be applied to endoscopes of other types.

It will further be appreciated that the preferred embodiments described above are cited by way of example, and the fill scope of the invention is limited only by the claims.

What is claimed is:

1. A video endoscope, comprising:

a generally rigid, elongate insertion member, having distal and proximal ends;

a video camera head fixed at the distal end of the insertion member; and a sheath, which fits over and covers the insertion member, the sheath having a distal portion covering the video camera head, at least a section of which distal portion is substantially transparent, wherein the distal portion of the sheath comprises a narrowed tip, which facilitates insertion of the endoscope through the anus, and wherein the narrowed tip comprises two or more leaves, which are closed during insertion through the anus and open apart after insertion to expose the transparent section of the distal portion of the sheath.

2. An endoscope according to claim 1, wherein to open the leaves, the sheath is shifted in a proximal direction drawn relative to the insertion member.

3. A video endoscope, comprising:

a generally rigid, elongate insertion member, having distal and proximal ends;

a video camera head fixed at the distal end of the insertion member; and a sheath, which fits over and covers the insertion member, the sheath having a distal portion covering the video camera head, at least a section of which distal portion is substantially transparent, wherein the sheath contains a working channel passing longitudinally therealong, and wherein the sheath comprises a one-way valve within the working channel, for preventing back-flow of fluid therethrough.

4. A method of endoscopic inspection, comprising:

providing an elongate, generally rigid insertion member having a video camera head at a distal end of the member;

fitting a disposable sheath over the member, such that the camera head is covered by a substantially transparent portion of the sheath;

inserting the insertion member, covered by the sheath, into a body cavity of a subject; and receiving video images within the body cavity from the camera head, wherein fitting the sheath comprises fitting a sheath having a narrowed tip, and wherein inserting the member comprises first inserting the narrowed tip into the cavity, and comprising the narrowed tip after to expose the substantially transparent of the sheath covering the camera head.

5. A method according to claim 4, wherein opening the narrowed tip comprises shifting at least a portion of the sheath in a proximal direction over the insertion member so as to separate two or more leaves that meet to form the narrowed tip.

* * * * *